(12) United States Patent
Chen et al.

(10) Patent No.: US 8,871,743 B2
(45) Date of Patent: Oct. 28, 2014

(54) BACTERIAL CELLULOSE COMPOSITE WITH CAPSULES EMBEDDED THEREIN AND PREPARATION THEREOF

(75) Inventors: Pei-Ying Chen, Hsinchu (TW); Jinn-Tsyy Lai, Hsinchu (TW); Hsu-Chou Hsiao, Hsinchu (TW); Yan-Hwa Chu, Hsinchu (TW); Chii-Cherng Liao, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 609 days.

(21) Appl. No.: 13/137,456

(22) Filed: Aug. 17, 2011

(65) Prior Publication Data

US 2012/0308649 A1 Dec. 6, 2012

(30) Foreign Application Priority Data

Jun. 2, 2011 (TW) .............................. 100119460 A

(51) Int. Cl.
| | | |
|---|---|---|
| *A61K 9/28* | (2006.01) | |
| *C08B 1/04* | (2006.01) | |
| *C12P 1/04* | (2006.01) | |
| *C12P 19/04* | (2006.01) | |
| *A61K 9/50* | (2006.01) | |
| *A61K 9/70* | (2006.01) | |
| *A23L 1/30* | (2006.01) | |
| *C12N 11/04* | (2006.01) | |
| *A61K 47/38* | (2006.01) | |

(52) U.S. Cl.
CPC ............... *C12P 19/04* (2013.01); *A61K 9/7007* (2013.01); *C12P 1/04* (2013.01); *A23L 1/3014* (2013.01); *A61K 9/5036* (2013.01); *C12N 11/04* (2013.01); *A61K 47/38* (2013.01)
USPC .............................. 514/57; 536/1.11; 536/124

(58) Field of Classification Search
CPC ................................ C08B 1/04; A61K 9/2866
USPC ......................................................... 536/1.11
See application file for complete search history.

(56) References Cited

U.S. PATENT DOCUMENTS 5,766,907 A * 6/1998 Chang et al. .................. 435/178
8,029,821 B2 * 10/2011 Hayakawa et al. ........... 424/451

FOREIGN PATENT DOCUMENTS

JP            3159091 U  *  5/2010
WO    WO 2007063854 A1  *  6/2007

OTHER PUBLICATIONS

The Kharkwal et al reference ("World Journal of Pharmacy and Pharmaceutical Science", Biodegradable Capsules: A Review, vol. 2, Issue 6, 4474-4484, Aug. 21, 2013) is only cited as an evidentiary reference to show that polysaccharide capsules are biodegradable (see p. 4475, line 12).*
Pei-Ying Chen, et al., *Inspection and Discussion about Embedding Technique in Bacterial Cellulose Preparation*, Taiwan Food Technology Society 40th Annual Meeting, Taichung, Taiwan, Dec. 3, 2010.

* cited by examiner

*Primary Examiner* — Brandon Fetterolf
*Assistant Examiner* — Everett White
(74) *Attorney, Agent, or Firm* — Bacon & Thomas, PLLC

(57) ABSTRACT

A composite of bacterial cellulose and capsules embedded therein is prepared, for example calcium alginate capsules encapsulating functional components being discretely embedded in a matrix of *Gluconacetobacter xylinus* cellulose. The functional components may be drugs, probiotics or nutrients, such as fungal polysaccharide.

20 Claims, No Drawings

BACTERIAL CELLULOSE COMPOSITE WITH CAPSULES EMBEDDED THEREIN AND PREPARATION THEREOF

FIELD OF THE INVENTION

The invention relates to a bacterial cellulose composite with capsules embedded therein and preparation thereof, and more particularly to a composite of calcium alginate capsules encapsulating functional components being discretely embedded in a matrix of *Gluconacetobacter xylinus* cellulose; the functional components may be drugs, probiotics, or nutrients, such as fungal polysaccharides.

DESCRIPTION OF PRIOR ART

The bacterium *Gluconacetobacter xylinus* (or used to be called *Acetobacter xylinum*) is able to produce white gelatinous bacterial cellulose (BC) by fermentation, which is commonly called Nata or Nata de coco, and possesses high concentration of cellulose, nano-scale structure, and high mechanical strength. Nata de coco is widely applied in foods, and the applications can be divided into three categories including snack foods, functional foods, and food additives. Nata de coco is often used in the snack foods because it not only tastes chewy and smooth, but also has an appealing translucent white appearance. It can also be mixed with a variety of colors and flavors and is highly shapeable, which makes it ideal for applications in products like jellies, canned foods, and beverages. In addition, bacterial cellulose can be cut up, homogenized and used as food additives, because it is found to have high water retention capacity, low viscosity, and is resistant to acid and heat. Therefore, it is often used as emulsifiers, stabilizers, fillers, and texture modifiers in the food additives, and commonly added as melting-resistant agents in ice creams, as flavoring sauces, as emulsifiers in margarine, or as forming agents in vegetarian meats, sausages, or meatballs. In regard to the functional foods, Nata de coco is often used as a dietary fiber therein, because it is not absorbed by the human body and makes people feel full after ingestion, and also increases intestinal tract movements that are beneficial in preventing constipation and colorectal cancers. Hence it is commonly used to develop low-calorie dietary and supplementary foods.

Encapsulation refers to the chemical or physical process of wrapping active components inside of a polymer material, and is important in preserving and providing controlled release of the active components, which subsequently helps deliver the components into the human body timely. The applications, materials, and techniques related to encapsulation have been extensively disclosed before. Microbial polymer matrix encapsulation is a newly developed technology. The hydroxyl polymers of biological substances that are most commonly used for encapsulation are alginate, polyacrylamide, carrageenan, agar, or agarose, in which only alginate and carrageenan can be easily shaped into a sphere along with the encapsulated substances. This is achieved by ionotropic gelling, which is done by dripping sodium alginate into a calcium ion solution, and by dripping carrageenan into a potassium ion solution.

In regard to selecting encapsulation materials, calcium alginate is preferable because it is convenient, non-toxic, has good bio-compatibility, and of low costs (Sheu and Marshall, 1993, J. Food Sci. 54: 557-561). Alginate is a straight-chain heteropolysaccharide derived from the D-mannuronic acid and L-guluronic acid of various algae extracts. The supportive characteristic of alginate is intimately related to the composition and sequence of L-guluronic acid and D-mannuronic acid. Divalent cations like $Ca^{2+}$ tend to bind with polymers of L-guluronic acid (Krasaekoopt et al., 2003, Int. Dairy J. 13: 3-13). Moreover, calcium alginate has another advantage in that the diffusion of calcium ions therefrom leads to the dissolution of calcium alginate, which in turn releases the encapsulated microbes into the digestive tract.

Chinese patent CN100460020 C discloses a method for preparing an inter-adhesion film made of multiple layers of *Gluconacetobacter xylinus* cellulose, which comprises the steps of culturing *Gluconacetobacter xylinus* in a liquid medium statically for 6-10 days to form a superficial film; adding a culturing liquid slowly on top of the film by using a dripping tube; repeating the slow addition of the culturing liquid every 5-6 days until the film reaches an average thickness of 3-8 mm. The multiple-layer bacterial cellulose film can then be used as a medical dressing.

Though the general encapsulation materials like sodium alginate, carrageenan, and agar are good for enclosing functional components, they are disadvantaged in having softer texture and thus easily damaged in following processing steps, which consequently harms the quality and quantity of the final products. Moreover, the encapsulated products often have capsule walls damaged from chewing or digestion, which causes the enclosed functional components to leak out prematurely.

As far as the inventors of this invention knows, a composite made from combining cellulose and capsules has not been developed until now, and the inventors have firstly prepare a bacterial cellulose composite having capsules embedded therein, so as to reduce the occurrence of capsule walls damaged by external forces.

SUMMARY OF THE INVENTION

An objective of the present invention is to provide a bacterial cellulose composite having capsules embedded therein, which comprises a bacterial cellulose matrix and a plurality of capsules being discretely embedded in said matrix, wherein said capsules include a core functional component and bio-degradable polymeric shells for enclosing said functional component.

Another objective of the invention is to provide a method for preparing a bacterial cellulose composite having capsules embedded therein, comprising:

providing a plurality of capsules, wherein said capsule includes a core functional component and a bio-degradable polymeric shell for enclosing said functional component;

providing a reaction tank and a sheet-like bacterial cellulose therein, wherein said sheet-like bacterial cellulose has a thickness of 2-10mm;

discretely placing the plurality of capsules on a top surface of said sheet-like bacterial cellulose, and then adding a liquid medium inoculated with bacteria on said top surface; or adding a liquid medium inoculated with bacteria on said top surface first, then discretely placing the plurality of capsules thereon, wherein the liquid medium inoculated with bacteria is allowed to immerse said sheet-like bacterial cellulose, and a liquid surface thereof is 0.2-0.8 mm above the top surface of said sheet-like bacterial cellulose;

culturing the bacteria statically and under atmospheric condition for a period of time, thereby allowing new bacterial cellulose to form at an interface where a liquid surface of the medium is in contact with the atmosphere, and the newly formed bacterial cellulose is adhered to the top surface of the sheet-like bacterial cellulose;

adding a liquid medium on top of the newly formed bacterial cellulose, and culturing the bacteria statically and under atmospheric condition for a period of time, thereby allowing another new bacterial cellulose to form at an interface where a liquid surface of the medium is in contact with the atmosphere, and the another newly formed bacterial cellulose is adhered to a top surface of the newly formed bacterial cellulose sheet-like bacterial cellulose thereunder, and repeating this step until the plurality of capsules are embedded in a matrix of bacterial cellulose formed from the sheet-like and newly formed bacterial cellulose.

The bacterial cellulose is preferably Gluconacetobacter xylinus cellulose.

The bio-degradable polymer is preferably calcium alginate, carrageenan, agar, agarose, or polyacrylamide. The bio-degradable polymer is more preferably calcium alginate.

The functional component is preferably a drug, probiotic, or nutrient.

The functional component is more preferably fungal polysaccharide, such as *Ganoderma lucidum* polysaccharide, *Antrodia camphorata* polysaccharide, *Coriolus versicolor* polysaccharide, or a mixture thereof.

The capsules are preferably 1-10 mm in diameter.

Preferably in the preparation method of the invention, the sheet-like bacterial cellulose is 3-5 mm in thickness, the capsules are 2-3 mm in diameter, and a liquid surface of the liquid medium inoculated with bacteria is 0.5 mm above the top surface of the sheet-like bacterial cellulose.

The preparation method of the invention also preferably comprises the following steps for preparing the plurality of capsules:

mixing a sodium alginate solution with a solution of fungal polysaccharide to obtain a mixed solution, wherein the concentration of fungal polysaccharide and sodium alginate in the mixed solution is 0.06-0.15% and 1.0-2.5%, respectively;

adding said mixed solution quantitatively into a calcium chloride solution, wherein the concentration of calcium chloride solution is 2.0-5.0%; and continuing to stir the solution for a period of time to result in capsules of fungal polysaccharides.

In the preparation method of the invention, the liquid medium added onto the newly and the another newly formed bacterial cellulose is preferably at a rate of $2.1 \times 10^{-3}$ to $5.4 \times 10^{-3}$ mL/cm$^2$·hr.

DETAILED DESCRIPTION OF PREFERRED EMBODIMENTS

Although the techniques for using alginate to enclose functional components and statically culture *Gluconacetobacter xylinus* cellulose are both already known in the industry, a composite made from both had not been successfully attempted until a disclosure is made in this invention. Relevant embodiments and comparisons are used to illustrate the problems encountered by the inventor in attempting to prepare a bacterial cellulose composite with capsules embedded therein, and the corresponding solutions.

Preparation 1: The Preparation of Capsules

The aqueous solutions of polysaccharides, sodium alginate, and CaCl$_2$ were firstly subjected to autoclaving for sterilization, and then used to prepare capsules under sterile conditions according to the following steps.

Mixed the aqueous solutions of polysaccharides (the concentration is 0.9%) and sodium alginate (the concentration is 5%) together and stirred evenly, took caution to prevent bubbles from forming. Added the mixed solution drop-by-drop into a stirring aqueous solution of 100 mL 5% CaCl$_2$ by using a syringe or dripping tube, and continued to slowly stir the solution for 5 minutes after the addition to allow it to solidify. The prepared capsules (with a diameter of 2-3 mm) were then washed with sterile water and stored away for later use.

Preparation 2: The Cultivation of *Gluconacetobacter xylinus* and the Preparation of Sheet-Like *Gluconacetobacter xylinus* Cellulose

| YE medium | |
|---|---|
| Sucrose | 50 g/L |
| Enzyme extracts | 5 g/L |
| (NH$_4$)$_2$SO$_4$ | 5 g/L |
| KH$_2$PO$_4$ | 3 g/L |
| MgSO$_4$·7H$_2$O | 0.05 g/L |

Took the strain of *Gluconacetobacter xylinus* preserved in a glycerol stock frozen at -80° C., and allowed it to be activated and cultured on a liquid medium at 30° C., so as to obtain a bacterial liquid of activated *Gluconacetobacter xylinus*.

Transferred 5% of the bacterial liquid of activated *Gluconacetobacter xylinus* to the YE medium by using a sterile pipette, then statically cultured the bacteria at room temperature for several days, until sheet-like *Gluconacetobacter xylinus* cellulose having a thickness of 3-5 mm was obtained. Subjected the cultured bacterial cellulose that was mixed with culture medium to filtration, so as to separate solids therein from the liquid medium; this was followed by immersing the solids with deionized water, and then stirring and centrifuging the resulted mixture. Replaced the deionized water until the color of the medium was completely removed, then centrifuged and dehydrated the mixture before immersing it in 1.0% NaOH solution, and boiling for 30 minutes to remove *Gluconacetobacter xylinus*. Subsequently, allowed the solution to cool, and then centrifuged again to remove the alkaline solution. Repeatedly washed the bacterial cellulose with deionized water until the pH turned neutral and ready for later use (George et al., 2005). In addition to cultivation by oneself, said sheet-like bacterial cellulose can also be purchased commercially.

Comparison 1: Directly Generating *Gluconacetobacter xylinus* Cellulose on the Culture Medium Having Capsules Sufficiently mixed a 0.9% polysaccharide solution with a 5% sodium alginate solution at different ratios to prepare capsules; obtained and placed 5 g of capsules in a flask with 10 mL of the YE medium, followed by inoculation with an inoculum size of 10% and static cultivation at 30° C. The addition of polysaccharides did not affect the growth of bacterial cellulose by *Gluconacetobacter xylinus*. After cultivation for 7 days, surfaces of the capsules were covered with a film of bacterial cellulose, but the bacterial cellulose film formed at the interface where the YE medium was in contact with the atmosphere did not adhere to said surfaces of the capsules, and was easily separated therefrom. When measuring the humid weight and gross polysaccharide concentration in the samples (Dubois et al., 1956), it was found that when polysaccharides were mixed with 5% sodium alginate solution at a volume ratio between 1:1 - 1:4, in order to prepare a bacterial cellulose with polysaccharide capsules dispersed therein, the resulted dry samples contained 0.4403, 0.3514, 0.2727, and 0.2696 g/L of gross polysaccharide concentration, respectively. In comparison with the samples prepared by directly adding the polysaccharide solution during the static culture of bacterial cellulose in the YE medium, the polysaccharide concentration in the bacterial cellulose with polysaccharide capsules dispersed therein was significantly increased.

Comparison 2: Preparing Bacterial Cellulose Composite Having Capsules in a Liquid Medium with *Gluconacetobacter xylinus* Cellulose Films After inoculating 10 mL of YE medium with the bacteria and culturing for 3-5 days, a layer of thin cellulose film (approximately 1 mm in thickness) formed superficially. Subsequently, capsules were placed thereinto and new YE medium was added for further culturing. But the weight of the added capsules forced the superficial cellulose film down below the liquid surface, while the newly added medium allowed new cellulose films to be formed at the air-liquid interface, which caused the cellulose films to become divided, and impeded the adhesion between the cellulose and the capsules.

Embodiment 1: Preparing Bacterial Cellulose Composite Having Capsules on Sheet-Like *Gluconacetobacter xylinus* Cellulose Firstly placed sheet-like bacterial cellulose (with a thickness of 5 mm and a surface area of 38.5 cm$^2$) at the bottom of a flask, then added the YE medium that has been inoculated with *Gluconacetobacter xylinus*, ensured that the liquid surface of the medium is 0.5 mm above the top surface of the sheet-like bacterial cellulose before evenly placing 5g of capsules thereon. Statically cultured the sample at 30° C., and *Gluconacetobacter xylinus* then formed new bacterial cellulose at the air-liquid interface, which was adhered to the sheet-like bacterial cellulose underneath. Consequently, the liquid medium was added at fixed quantity in batch operation, which ensured that 2 mL of YE medium was added in drops every 24 hours to allow for further static culturing. The new bacterial cellulose then formed downwards, and completely enclosed the polysaccharide capsules after about 7 days of culturing; the total thickness of the bacterial cellulose composite increased to approximately 10-12 mm, and the polysaccharide concentration in the bacterial cellulose composite could reach 6.92%.

Embodiment 2: Effects of Sterilization Treatment to the Thermal Stability of Bacterial Cellulose Composites The final products of Embodiment 1 were subjected to sterilization treatment, which meant they were heated for sterilization at 121° C. in a steam autoclave for 15 minutes. After sterilization, the loss rates of functional components in bacterial cellulose composites having different thicknesses, and of different starting amounts of polysaccharide capsules were examined. It was revealed that when sheet-like bacterial cellulose with a thickness of 3 mm was used for the preparation, the total loss of polysaccharides for the resulted products of bacterial cellulose composite was 3.70% after sterilization. Whereas when sheet-like bacterial cellulose with a thickness of 8 mm was used for the preparation, the total loss of polysaccharides for the resulted products of bacterial cellulose composite was 0.02% after sterilization. After sterilization, the products of bacterial cellulose composite only appeared to have culturing medium released superficially and lighter in color, and the overall form and shape of the polysaccharide capsules were not changed significantly after the high-temperature and high-pressure sterilization. In addition, when 3 mm-thick sheet-like *Gluconacetobacter xylinus* cellulose and 10 g of polysaccharide capsules were used to prepare bacterial cellulose composites according to the method of Embodiment 1, the total loss of polysaccharides for the resulted products under the same sterilization conditions (heated at 121° C. for 15 minutes) was 1.23%.

The embodiments of the invention had showed that the method disclosed herein effectively increases the adhesion between polysaccharide capsules and bacterial cellulose. Moreover, the nano structure of the outer bacterial cellulose serves as a protective material for the polysaccharide capsules therein, which reduces possible damage to the polysaccharide capsules from the follow-up treatments, thereby effectively preserving the concentration of functional components in the products of bacterial cellulose composites.

In other experiments, the inventors also found that the bacterial cellulose composites with polysaccharide capsules prepared according to Embodiment 1 can inhibit the activeness of α-glucosidase, and the inhibition of α-glucosidase is positively related to the total polysaccharide concentration thereof. For example, if the total polysaccharide concentration of a product of bacterial cellulose composites is 2.70%, the α-glucosidase inhibition rate will reach 17.8%; if the total polysaccharide concentration is 4.40%, the inhibition rate will be 41.4%, and if the total polysaccharide concentration is 6.49%, the inhibition rate will reach 61.9%. Similar effects can also be achieved by using a single product of the bacterial cellulose composite with a fixed total polysaccharide concentration, but the amount of the composite product has to be modified in order to adjust its level of inhibition on α-glucosidase.

The preferred embodiments of the invention described above are meant to illustrate the invention, and are not to be used to limit the scope of the invention; those skilled in the art should be able to make modifications and changes to the embodiments without departing from the scope of the invention.

What is claimed is:

1. A bacterial cellulose composite having capsules embedded therein, comprising a bacterial cellulose matrix and a plurality of capsules being discretely embedded therein, wherein said capsule comprises a core functional component and a bio-degradable polymeric shell enclosing said functional component.

2. The composite of claim 1, wherein said bacterial cellulose is *Gluconacetobacter xylinus* cellulose.

3. The composite of claim 1, wherein said bio-degradable polymer is calcium alginate, carrageenan, agar, agarose, or polyacrylamide.

4. The composite of claim 3, wherein said bio-degradable polymer is calcium alginate.

5. The composite of claim 1, wherein said functional component is a drug, probiotic, or nutrient.

6. The composite of claim 5, wherein said functional component is a fungal polysaccharide.

7. The composite of claim 6, wherein said fungal polysaccharide is *Ganoderma lucidum* polysaccharide, *Antrodia camphorata* polysaccharide, *Coriolus versicolor* polysaccharide, or a mixture thereof.

8. The composite of claim 1, wherein said capsules are 1-10 mm in diameter.

9. A method for preparing a bacterial cellulose composite having capsules embedded therein, comprising:
   providing a plurality of capsules, wherein said capsule includes a core functional component and a bio-degradable polymeric shell for enclosing said functional component;
   providing a reaction tank and a sheet-like bacterial cellulose therein, wherein said sheet-like bacterial cellulose has a thickness of 2-10 mm;
   discretely placing the plurality of capsules on a top surface of said sheet-like bacterial cellulose, and then adding a liquid medium inoculated with bacteria on said top surface; or adding a liquid medium inoculated with bacteria on said top surface first, then discretely placing the plurality of capsules thereon, wherein the liquid medium inoculated with bacteria is allowed to immerse said sheet-like bacterial cellulose, and a liquid surface thereof is 0.2-0.8 mm above the top surface of said sheet-like bacterial cellulose;

culturing the bacteria statically and under atmospheric condition for a period of time, thereby allowing new bacterial cellulose to form at an interface where a liquid surface of the medium is in contact with the atmosphere, and the newly formed bacterial cellulose is adhered to the top surface of the sheet-like bacterial cellulose;

adding a liquid medium on top of the newly formed bacterial cellulose, and culturing the bacteria statically and under atmospheric condition for a period of time, thereby allowing another new bacterial cellulose to form at an interface where a liquid surface of the medium is in contact with the atmosphere, and the another newly formed bacterial cellulose is adhered to a top surface of the newly formed bacterial cellulose sheet-like bacterial cellulose thereunder, and repeating this step until the plurality of capsules are embedded in a matrix of bacterial cellulose formed from the sheet-like and newly formed bacterial cellulose.

10. The method of claim 9, wherein said bacterial cellulose is *Gluconacetobacter xylinus* cellulose.

11. The method of claim 9, wherein said bio-degradable polymer is calcium alginate, carrageenan, agar, agarose, or polyacrylamide.

12. The method of claim 11, wherein said bio-degradable polymer is calcium alginate.

13. The method of claim 9, wherein said functional component is a drug, probiotic, or nutrient.

14. The method of claim 13, wherein said functional component is a fungal polysaccharide.

15. The method of claim 14, wherein said fungal polysaccharide is *Ganoderma lucidum* polysaccharide, *Antrodia camphorata* polysaccharide, *Coriolus versicolor* polysaccharide, or a mixture thereof.

16. The method of claim 14, wherein the plurality of capsules are prepared by a process comprising the following steps:

mixing a sodium alginate solution with a solution of fungal polysaccharide to obtain a mixed solution, wherein concentrations of the fungal polysaccharide and the sodium alginate in the mixed solution is 0.06-0.15% and 1.0-2.5%, respectively;

adding said mixed solution quantitatively into a calcium chloride solution, wherein a concentration of the calcium chloride solution is 2.0-5.0%; and continuing to stir the solution for a period of time to result in capsules of fungal polysaccharide.

17. The method of claim 9, wherein said capsules are 1-10 mm in diameter.

18. The method of claim 9, wherein the sheet-like bacterial cellulose is 3-5 mm in thickness, the capsules are 2-3 mm in diameter, and a liquid surface of the medium is 0.5 mm above the top surface of the sheet-like bacterial cellulose in the reaction tank.

19. The method of claim 9, wherein the liquid medium added onto the newly formed bacterial cellulose is $2.1 \times 10^{-3}$ to $5.4 \times 10^{-3}$ mL/cm²·hr.

20. The method of claim 9, wherein the liquid medium added onto the another newly formed bacterial cellulose is $2.1 \times 10^{-3}$ to $5.4 \times 10^{-3}$ mL/cm²·hr.

* * * * *